United States Patent [19]

Grichnik

[11] 4,037,586
[45] July 26, 1977

[54] ELECTROENCEPHALOGRAPH DISPLAY
[76] Inventor: James A. Grichnik, 1107 S. Aldine, Park Ridge, Ill. 60068
[21] Appl. No.: 676,721
[22] Filed: Apr. 14, 1976
[51] Int. Cl.² .............................................. A61B 5/04
[52] U.S. Cl. ........................... 128/2.1 B; 346/33 ME
[58] Field of Search ............ 128/2.1 B, 2.1 M, 2.1 R, 128/2.06 B, 2.06 G; 346/33 ME

[56] References Cited
U.S. PATENT DOCUMENTS

| 2,409,033 | 10/1946 | Garceau | 128/2.1 B |
| 2,712,309 | 7/1975 | Offner | 128/2.1 B |
| 2,933,364 | 4/1960 | Campbell | 128/2.1 B |
| 3,090,844 | 5/1963 | Streu | 128/2.1 B X |
| 3,623,477 | 11/1971 | Trent | 128/2.1 B |
| 3,910,258 | 10/1975 | Pisarski | 128/2.1 B |

OTHER PUBLICATIONS

Grieco, "A New Apparatus . . . Physiology," Med. & Biol. Eng., vol. 9, No. 6, pp. 705–710, 1971.

Primary Examiner—Robert W. Michell
Assistant Examiner—Lee S. Cohen
Attorney, Agent, or Firm—Leo Aubel

[57] ABSTRACT

An electroencephalograph (EEG) instrument or system including a visual display panel actuated in response to digital signals for indicating the particular pattern in which the electrodes connected to the patient are processed to provide the desired output signals.

6 Claims, 3 Drawing Figures

U.S. Patent  July 26, 1977  4,037,586
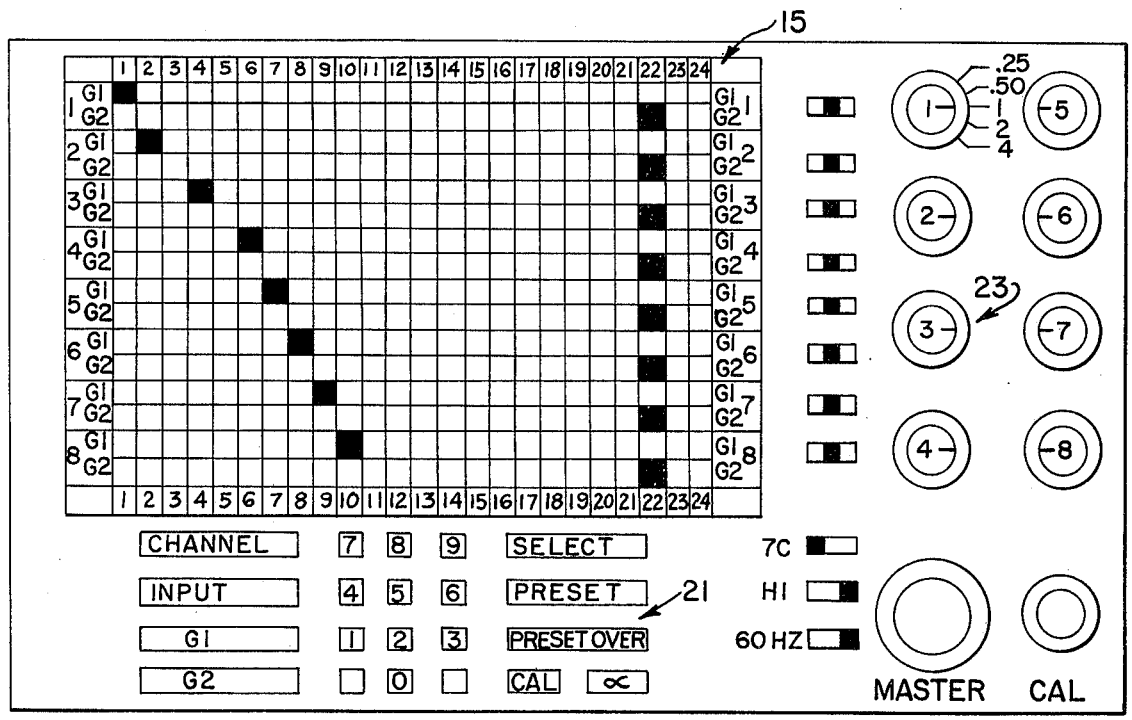
FIG—1.
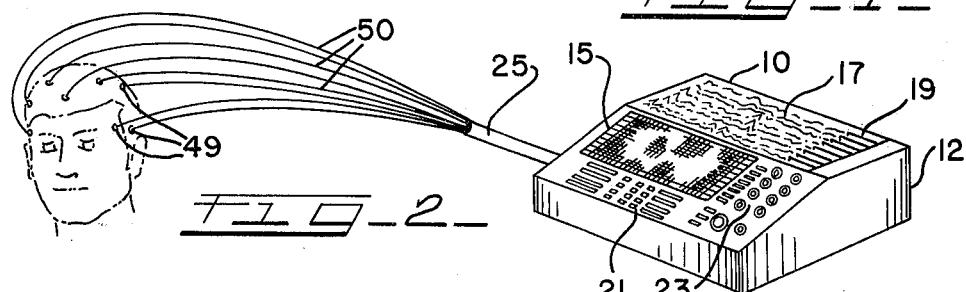
FIG—2.
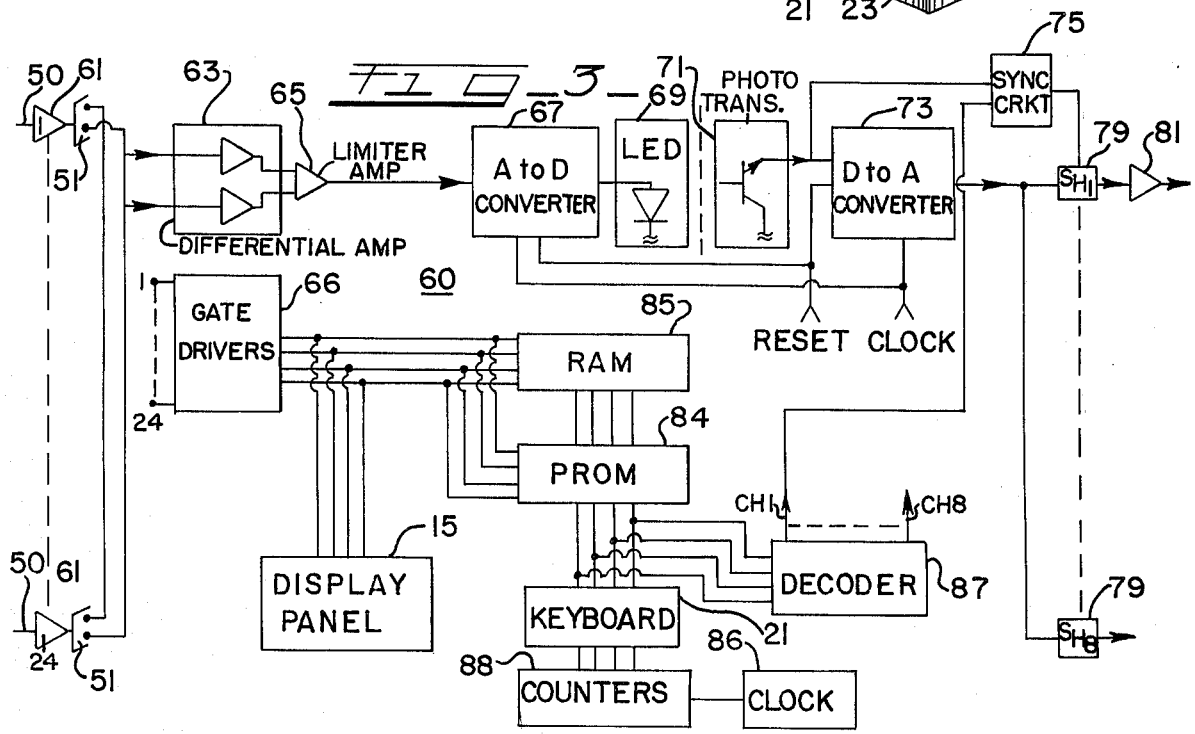
FIG—3.

ELECTROENCEPHALOGRAPH DISPLAY

BACKGROUND OF THE INVENTION

This invention relates to digital electroencephalograph (EEG) instruments or systems, and more particularly, to an EEG system including the provision of a visual display panel for indicating to an operator the particular pattern in which electrodes connected to the patient are being selectively processed to provide the desired signals.

Electroencephalographs that are in general use employ an analog signal generated by the brain for direct transmission to a recorder to obtain an appropriate readout of the signal. When the general procedure requires individual selection of pairs of electrodes or signal receiving terminals, the prior art units can be satisfactory. However in actual operating conditions, insufficient time is available to make such individual selections of the electrodes and therefore, electroencephalographs normally record a montage of wave forms comparing a series of selected electrodes and then switch to a different series of electrodes for recording comparisons of different electrodes. It is not unusual that up to ten such different runs comparing different sets of electrodes are recorded for a given patient. Thus, it is obvious that individual selections of different arrays of electrodes can require an excessive amount of time; and therefore, is impractical.

To overcome this problem, mechanical switches are in general use for selecting different montages of electrodes to couple to an associated output amplifier. These mechanical switches have preset stations by which the switch may select various combinations of electrodes for coupling and recording purposes.

In presently available EEG instruments there is no manner apparent on the operator control panel by which the operator may ascertain the actual montage of electrodes or the patterns in which the electrodes are being scanned to couple the signals to the output circuits. And, it is presently difficult if not impossible to correctly record the desired montage with absolute assurance of being correct in that selection.

The present invention overcomes this problem by providing a display console which visually provides the operator with a representation of the scanning pattern or montage. With this visual display, the operator can immediately confirm the pattern selection or scanning procedure being selected, at the time it is selected, thus providing a check on the internal wiring of the instrument.

Prior art electroencephalographs are normally analog signal devices, and have not fully utilized state of the art miniaturized electronic components and circuits and have remained bulky and relatively immobile. Increasing the capacity of prior art EEG instruments is difficult because of the increase in complexity, that is, the mass of extra wiring, connections, terminations, etc. to provide the corresponding desired increase in capacity of the instrument.

Accordingly, the present invention is premised on the important concept of providing an EEG system utilizing digital circuitry; and, the provision of display which is made feasible by converting the analog signal received from the electrode on a patient into a digital signal for processing. This analog to digital conversion not only makes possible a display panel, but also increases the capabilities of an electroencephalograph instrument. The conversion to a digital signal enables more efficient and less bulky state of the art electronics to be utilized, and also makes possible a direct connection to a data processor to gain the advantages of its comparative analytical abilities.

As mentioned above, the conversion to a digital signal allows the provision of an operator display panel to incorporate visual and mechanical features which were heretofore not commercially or practically possible. Through the use of a digital signal, a display of each and every electrode combination in use at a certain point in time can be effectuated for informing the operator of that particular combination.

Further advantages are found in the conversion to a digital signal in that it allows the expansion of the capability of the instrument without the corresponding increase in size and components. If it becomes desirable to expand the capabilities of a particular instrument by the addition of more additional electrodes, these electrodes may be added with the mere addition of a minimum of wiring and no increase in overall panel or instrument size. This decrease in size requirements for the instrument makes possible a truly portable instrument weighing approximately 25 to 30 pounds in contrast to the present sixty to seventy pound bulky instrument currently in general use.

Accordingly, it is a principal object of the present invention to provide a visual display panel to define, identify, and confirm the pattern in which the electrodes are electrically activated or scanned to provide a selected output.

It is another object of the present invention to convert the analog signal generated by the patient and transmitted by appropriate electrodes into a digital signal for use in an electroencephalograph instrument.

Still another object of the present invention is the use of digital signals to simplify the electronic circuitry of an electroencephalograph.

A further object of the subject invention is the reduction in size of an electroencephalograph to make it lightweight and portable and conveniently expandable in capacity without a corresponding increase in size by the use of digial components.

Further objects of the invention together with additional features contributing thereto and advantages accruing therefrom will be apparent from the following description of one embodiment of the invention when read in conjunction with the accompanying drawings wherein:

DESCRIPTION OF THE DRAWINGS

FIG. 1 is a plan view of one embodiment of the matrix display in accordance with the invention;

FIG. 2 is an isometric view of a display console in accordance with the invention; and FIG. 3 shows a block diagram circuit such as may be employed in the inventive system.

DESCRIPTION OF THE INVENTION

Refer first to FIG. 2 which depicts an electroencephalograph instrument or system (EEG)10 in accordance with with invention. The EEG system 10 is generally similar to other prior art instruments on the market, and is generally related to the structure and circuitry disclosed in, for example, in the relatively recently issued U.S. Pat. Nos. 3,900,215 to E. R. Johns; 3,910,258 to Pisarski, et al; and 3,924,606 to Silva, et al.

FIG. 2 depicts the usual electrodes 49 which electrically couple to the head of a patient. As is known, in prior art systems, corresponding electrodes couple the analog signals from the patient to drive the pen recorders and provide tracings 17 of the patient's brain response or electroencephalograms. In contrast, in the inventive EEG system 10, the analog signals on the electrodes 49 are coupled through respective conductive leads 50 to an analog to digital converter to permit the digital processing of the signal from the electrodes. Subsequently, the digital signals are converted to analog signals to drive the pen recorders.

Refer now to FIG. 3 which depicts in block diagram form, a digital control circuit, generally labeled as 60, for a twenty-four electrode, eight channel EEG system 10 such as shown in FIG. 2. The provision of circuitry for converting the analog data obtained from the electrodes 49 when coupled to the patient into digital data enables control circuitry to be provided to establish the visual presentation on a display panel 15 to show the selection of the scan pattern or montage as discussed above. The digital control circuitry 60, is per se, part of the invention only in that it discloses one of a number of digital circuits which could be used in the EEG system 10; that is, the state of the art is such that any number of different digital circuits and components, commonly available, could be utilized to convert analog signals obtained from the electrodes 49 into digital data. Accordingly, the circuit 60 of FIG. 3 is merely representative of one useful circuit for this purpose. It should be further understood at the outset, that the embodiment of the circuit 60 constructed comprise all state-of-the-art components readily available in the market place.

As mentioned above, and as is well known in the art, the electrodes are electrically coupled to the head of the patient, and the signals developed at the electrodes are coupled through the associated electrically conductive leads 50 through appropriately shielded channels, generally labeled 25, to the control or operating console 12 of the inventive EEG system 10. Also as mentioned above, data or information signals obtained from the EEG system 10 are similar to that obtained from other presently available systems. The circuitry of the present invention, however, converts the analog signal on the electrodes 49 to a digital format, processes the signal and then converts the digital signals back to an analog signal. The foregoing analog to digital and digital to analog conversion and techniques are well known in the art.

As is known, in EEG systems of the type herein described it is desired to concurrently detect and compare the signals on two selected electrodes 49 to provide a differentiated signal. The electrodes 49 are controllably scanned and sampled through electronic gates, generally labeled 51, which are driven or selectively controlled by suitable gate drivers 66. For simplicity in the drawing, driving gates 51 have been indicated as mechanical switches, however, it will be understood that known electronic circuits perform the switching function. The gate drivers 66 selectively drive or close the gates 51 to scan the electrodes in the desired pattern or sequence; that is, to selectively connect each two of the electrodes to a differential amplifier 63. The gate driver 66 thus concurrently connects the signals from two electrodes 49 through a differential amplifier circuit 63, to provide a differential output to a limiter amplifier 65. The signal from the amplifier 65 is coupled to an analog to digital (A to D) converter 67.

The output of an A to D converter 67 is coupled such as through an opto-electronic coupling device, comprising an LED 69 circuit, (light emitting diode), and a photo sensitive transistor circuit 71 to a digital to analog converter 73. The LED 69 and photo sensitive transistor 71 provide signal isolation between patient and the output circuits such as for driving the recording pens 19, see FIG. 2.

The output from the photo sensitive transistor 71 is coupled to a digital to analog converter 73 which converts the digital signal back to an analog signal corresponding to the initial signal coupled from the respective electrodes 49 to drive the recorder pens 19 of the EEG system 10. It should be appreciated that the digital signal output from the A to D converter 67 can also be conveniently coupled to a data processor (not shown) to process the information in any manner desired such as by comparing with stored data, etc., as is well known in the art.

The keyboard 21 indicated in block diagram is shown in more detail in FIG. 1. It is a principal feature of the invention that the keyboard 21 enables the display panel 15 to visually indicate on a matrix display, the particular scanning pattern initiated by the keyboard actuation. That is, the operator can see what the scanning pattern or montage actually is. As will be described hereinbelow, in a first mode of operation, data may be entered into the keyboard 21 by manually depressing the selected keys. In the first mode of operation, the keyboard control data selected is coupled to a random access memory (RAM) 85 to control the gate drivers 66 and thus, the scanning pattern of the electrodes 49.

The system clock 86 and the counters 88 provide the timing control pulses for the system. In a second mode of operation, the keyboard 21, selects a programmed actuation by activating the program read only memory (PROM) 84 which is programmed to provide preselected scan patterns. A decoder 87 of any suitable known type, is such as indicated in the keyboard 21 and memory circuits to provide an output to a known type of synchronizing circuit 75 to enable synchronization and proper timing of the data sample and hold circuits with the scanning operation of the input gates 61. A number of suitable synchronization techniques and circuits are well known in the art. The output of the sample and hold circuits generally labeled 79 and individually labeled SH1-SH8 are connected through suitable amplifiers 81 to drive the recording pens 19, see FIG. 2.

A principal feature of the invention, that is, display panel 15 operable in conjunction with the keyboard 21 will now be discussed. As shown in FIGS. 1 and 2, the display panel 15 of console 12 comprises a matrix or grid of individual lamps or lights positioned in a cartesian coordinate system. The lamps are selectively caused to light to indicate a particular scanning pattern selected by the apparatus of FIG. 3. Other matrix arrangements could be utilized; however, the X-Y coordinate matrix shown has been found to be practical and convenient.

In FIG. 1, the horizontal axis or axis of abscissas of the display panel matrix shows 24 positions to correspond to the twenty-four electrodes 49 in FIG. 2. The vertical axis or the axis of ordinates of the display panel 15 shows eight channels to correspond to the eight channels CH1-CH8 of FIG. 2, and two gates G1 and G2 provided for each channel. The channels correspond to the number of pen recorders 19, each of which provides a brain wave tracing. It should be understood at the outset that the display panel shown herein may be easily enlarged to accommodate more electrode positions and number of channels. The basic feature, however, remains the same, that is the invention provides actuating a lamp matrix to be representative of the exact pattern in which the electrodes are being scanned to provide information.

The keyboard 21 includes the respectively marked numerical keys 0 to 9; and, the special purpose keys including a channel key, input key, G1 and G2 keys, and keys for select, preset, preset over, calibrate and alpha. In addition, the display console 15 includes various other special control keys generally labeled 23 which keys are conventional and per se, do not form a part of the present invention.

In operation, the operator determines the type of pattern desired and depresses the select key to initiate the select operation. Next, the channel key may be actuated, and the particular channel number selected by actuating the proper numerical key. Next, the input key may be actuated to indicate electrode selection in conjunction with the proper numerical key. Next, the G1 gate key may be actuated to correspond to the selected channel and electrode. Finally, the second electrode of the pair and the gate G2 are selected.

For the example, the selection procedure for channel 1 in the showing in FIG. 1 would be as follows:

KEY ACTUATION

1. SELECT
2. CHANNEL
3. Numeral 1
4. INPUT
5. Numeral 1
6. Gate 1
7. Numeral 22
8. Gate 2

In the preset mode, the operator actuates the PRESET key to activate the PROM memory 84 which memory has been preset to establish a selected scanning pattern to directly control the scanning sequence. PROM 84 also actuates or lights up the display panel 15 to indicate the selected scanning pattern. Obviously, the particular PROM utilizied can be an interchangeable unit or different program from a more sophisticated PROM could be used, dependent on the various scanning patterns desired.

While the invention has been particularly shown and described with reference to a preferred embodiment thereof, it will be understood by those skilled in the art that various changes in form and details may be made therein without departing from the spirit and scope of the invention.

I claim:

1. A digital electroencephalograph system including a plurality of electrically responsive terminals connectable to a patient's head for obtaining electrical signals, electronic circuit means for scanning said terminals for obtaining analog electrical signals from said terminals in selectable format, means for converting said analog signals to data in digital format, means for providing visual display of the selected format in which the terminals are scanned and thus of the actual format in which the data is obtained, and means for converting said data into an output analog signal.

2. An EEG system as in claim 1 further including means for coupling said output analog signal to recording means.

3. A system as in claim 1 further including a programmable read only memory; means connecting said memory for providing a preset program to said electronic circuit means for scanning said terminals, and keyboard means for selectively actuating said memory.

4. A system as in claim 1 further including a random access memory, keyboard means, and manual actuable keys on said keyboard means connected to said electronic circuit means for selectively actuating said random access memory to provide formats for scanning said terminals.

5. A system as in claim 1 wherein said visual display means comprises lamps arranged in a panel to provide a pattern of lights corresponding to the format in which said terminals are being scanned.

6. A system as in claim 1 wherein said visual display means comprises a matrix of lamps arranged in cartesian coordinate relation, one axis of said coordinates indicating electrical signal channels, each of said channels including first and second gate means; the other axis of said coordinates representing the number of terminals connected in the circuit, and keyboard means connected to actuate said circuit and said matrix for causing said lamps in said matrix to be selectively lighted to thereby provide a visual representation of the pattern in which said terminals are being scanned.

* * * * *